United States Patent [19]
Gordon et al.

[11] Patent Number: 5,642,192
[45] Date of Patent: Jun. 24, 1997

[54] DUAL SPECTROMETER COLOR SENSOR

[75] Inventors: Daniel A. Gordon, Cupertino; Mark J. Alguard, Palo Alto, both of Calif.

[73] Assignee: Measurex Corporation, Cupertino, Calif.

[21] Appl. No.: 489,362

[22] Filed: Jun. 12, 1995

[51] Int. Cl.$^6$ .............................. G01J 3/42; G01N 21/86
[52] U.S. Cl. ..................... 356/328; 356/429; 356/72
[58] Field of Search ..................................... 356/319, 326, 356/328, 73, 72, 446, 429

[56] References Cited

U.S. PATENT DOCUMENTS

| | | | |
|---|---|---|---|
| 4,499,821 | 2/1985 | Lee | 356/319 |
| 4,659,193 | 4/1987 | Nagano | 359/387 |
| 5,047,652 | 9/1991 | Lisnyansky et al. | 356/429 |

FOREIGN PATENT DOCUMENTS 0087403  8/1983  European Pat. Off. .

OTHER PUBLICATIONS

PCT Search Report, Int. App. No. PCT/US96/09736, Dated Oct. 9, 1996.

*Primary Examiner*—F. L. Evans
*Attorney, Agent, or Firm*—Loeb & Loeb LLP

[57] ABSTRACT

Disclosed is an apparatus for measuring on-line the color and color-related properties of a moving sheet. Contrast ratio reflectance measurements are made for providing opacity corrections substantially in real time for a full color spectrum. An optical color sensor in accordance with the invention includes a pair of synchronized spectrometers, the first spectrometer being aligned to view a region of the sheet backed with a highly reflective ("white") material and the second spectrometer being aligned to view a region of the sheet backed with a highly absorptive ("black") material. The use of two spectrometers permits substantially simultaneous "black" and "white" measurements for a full color spectrum. The optical color sensing system further includes two light sources, a flashlamp and a continuously energized tungsten filament lamp. The color sensor further includes a sheet backing system including a rotatable standard wheel carrying a white standard tile. Provision is made to permit rotation of the standard wheel and to standardize the sensor off-sheet while maintaining isolation of the white standard tile from the paper mill environment. The sheet backing system includes a paper guide plate defining an annular vortex space into which air is introduced from a pressurized source. A low pressure region thereby produced in the vortex space draws the paper sheet toward the guide plate. At the same time, circulating air spirals outwardly from the vortex space to form a thin air film or air bearing between the sheet and the paper guide.

11 Claims, 12 Drawing Sheets

DUAL SPECTROMETER COLOR SENSOR

FIELD OF THE INVENTION

The present invention relates generally to sensors providing on-line, scanning measurements of such properties as color, whiteness, brightness and fluorescence of a traveling sheet of material such as paper.

BACKGROUND OF THE INVENTION

Opacity Correction

In the quality laboratory of a modern paper mill, color, brightness, whiteness, and fluorescence of the product are conventionally measured on a multiple sheet "pad" of the paper, rather than on a single sheet. If only a single sheet is measured, the results will be influenced by both the partial transparency of the sheet and the reflectance of the backing against which the sheet is observed. Furthermore, the "infinite pad" value is usually what the end customer is concerned with, since this is typically how the customer will view the end product. However, these measurement conditions cannot be reproduced in-situ in the manufacturing process, where an "on-line" color sensor can view only a single thickness of the product.

Two strategies have been employed to improve the agreement of on-line color measurements with laboratory "pad" measurements. The first strategy, an example of which is disclosed in U.S. Pat. No. 4,715,715, is to back the sheet with an opaque material which approximates the color and optical scattering power of the paper being manufactured. In effect, this strategy reproduces infinite pad conditions. The measurement error at each wavelength will be proportional to the mismatch between artificial and real "pad" spectral reflectance and inversely proportional to the square of the spectral transmittance of the single sheet. This strategy works well for sheets of medium to low transparency (<20%), since only modest agreement between backing and product is required. For less opaque paper or in the case of frequently changing product targets it is often difficult to keep the backing in close enough agreement with the product to insure good sensor performance.

The second strategy is to measure the sheet spectral reflectivity twice, once backed with a highly reflective (i.e., "white") material, and once backed with a highly absorptive (i.e., "black") material. From these independent measurements, the spectral transparency can be determined and the infinite pad spectral reflectivity calculated according to the Kubelka-Munk theory. An example of an apparatus for measuring dark and bright reflectances in succession is disclosed in U.S. Pat. No. 4,944,594. The apparatus of that patent includes a sheet backing system comprising an optical gating means that absorbs substantially all of the transmitted portion of the incident radiation when electronically switched to a dark state and reflects substantially all of the transmitted portion of the radiation when switched to a bright state. This approach does not require maintenance of product related backings and is therefore to be generally preferred. However, if the two measurements occur at significantly different times on significantly different parts of the paper, then the difference between the "black backed" and "white backed" spectral reflectivities may be due not only to the transparency of the sheet but to product (color and transparency) non-uniformity as well. If such variations are present, the calculation under the Kubelka-Munk theory will fail. On a modern paper machine, the web travels at 50 feet per second or more, and the sensor itself may be on a scanner moving 15 inches per second across the traveling sheet. In accordance with systems of the prior art in which the backing must be switched from "black" to "white" between these measurements, the measurements will thus inevitably be made on very different parts of the sheet. In these systems, the results of numerous reading sequences are typically combined in an attempt to average out the effect of product color non-uniformity. The final measurement update rate is then necessarily low and does not permit accurate, rapid control of color during fabrication of the paper.

Attempts have been made to make simultaneous "black" and "white" backed measurements. For example, U.S. Pat. No. 3,936,189 discloses a tristimulus colorimeter for on-line monitoring of the color, opacity and brightness of a moving web such as paper having an area illuminated by a light source. The colorimeter of the '189 patent includes four photometers each incorporating a filter to duplicate the ICI tristimulus functions for measuring the tristimulus values of the light incident on these detectors; a brightness detector having a 457 nm filter (brightness, according to the '189 patent, being defined as reflectance at a source wavelength of 457 nm); and an opacity detector fitted with a Y response filter. The '189 patent further includes a sheet backing element including a quartz "shoe" providing both black and white backgrounds. The black background is provided by a cavity under the quartz shoe while the white background is provided by a white stripe on the surface of the shoe. The photometers are so oriented that the optical axes of the four color tristimulus value detectors and the brightness detector are directed toward a portion of the illuminated area overlying the black background while the optical axis of the opacity detector is directed towards a portion of the illuminated area overlying the white stripe. The output of the opacity detector and the output of the tristimulus value detector providing the tristimulus Y measurement are used to provide a value of contrast ratio reflectance for correcting color luminosity or brightness to infinite pad backing. However, because the sensor of the '189 patent employs an opacity correction strategy that only corrects for one of the three color coordinates which is insufficient to fully define a color, a true color correction can only be estimated. Except for neutral colors, even the Y correction is in error since the Y-value is a weighted average over a wavelength band and the transparency correction is a non-linear function of "black" and "white" backed reflectivities which must be applied at each wavelength before computing the Y-value.

Accordingly, instead of simply a calculation of the luminosity or brightness of the sheet for infinite backing, what is needed is a wavelength-by-wavelength opacity correction before computing all color coordinates, that is, a full color correction for opacity at every wavelength. Moreover, such correction should be made in real time to permit immediate on-line adjustments to be made in the papermaking process.

Measurement of Fluorescent Properties

U.S. Pat. No. 4,699,510 discloses an on-line color sensor for measuring the color of a moving sheet of paper which contains fluorescent whitening agents (FWA). Fluorescent whitening agents typically absorb the violet and ultraviolet energies of incident light and re-emit these energies in the blue range of the visible spectrum to give the paper a whiter appearance. The '510 patent discloses techniques for determining the color spectrum of such treated paper if illuminated by a defined source such as the CIE D65 (North Sky Daylight) standard source. The D65 standard source has an energy distribution which, compared to other standard sources such as CIE source C, is relatively bright in the 300–400 nm range; consequently, paper with fluorescent whitening agents is likely to appear bluer if illuminated by a D65 source.

The color sensor of the '510 patent has two sources of illumination, one an ultraviolet source which emits light primarily in the excitation band of fluorescent whitening agents, the other a visible light source with an emission spectrum approximating a CIE standard source which also emits a significant amount of light in the UV or excitation range of FWA. The first source is rapidly switched on and off while the second source remains on continuously. Differences in data obtained while the first source is on and while it is off is used to compute the FWA efficiency or effective FWA concentration. Further, a corrected color spectrum can be determined which would be obtained if the sample were illuminated by a defined or standard source. Analysis of the spectrum of light reflected and emitted from the sheet is measured by a spectrometer which is periodically calibrated off-sheet by means of a plurality of standards carried on a stepper motor driven wheel under the sheet passline. The standards include a white standard moved into position by the stepper motor to calibrate the sensor. After calibration with the white standard, the color sensor reads the surface of a fluorescent standard sample with known fluorescent properties to determine the excitation energy in both the UV and incandescent sources and ultimately to obtain a color spectrum that is corrected to a true standard defined source. As the light sources age, however, the balance of UV to visible light spectra which characterizes the standard source changes. In systems of the prior art, compensation for this change is made by a UV blocking filter inserted part way into the flashlamp beam. By adjusting the physical position of the filter, the balance of the UV to visible light can be adjusted. It would be desirable to avoid the use of such moving parts.

Protection of Standardizing Tile

Backing systems of the prior art typically include a housing containing a rotatable block or wheel having three or more equiangularly spaced backing plates which may be selectively rotated by means of a stepper motor to bring backing plates—including plates with black and white surfaces to correct for various levels of opacity and for performing periodic standardization—into position opposite the optical sensing system.

Standardization is performed "off sheet" between scans, that is, with the heads of the scanner moved to one end of their travel. Typically, a tile with a white surface having a known reflective response is substituted for the paper surface and is presented to the incident beam produced by the optical sensing system. This periodic standardization procedure serves to correct for such disturbances and offsets as electronic circuit drift, aging of the source lamp and the accumulation of dirt or debris on the optical elements. The optical sensor system is thus calibrated during each such standardization procedure based on the known response of the system to the surface of the standard tile.

Increasing color sensor precision makes it more important to keep the white standard tile very clean and sealed off from the paper mill environment. The rotatable block or wheel backing systems presently in use do not adequately protect the standard tile from the build up of dust or debris on the surface of the tile. The accumulation of foreign matter on the standard tile surface alter the reflectance properties of the surface. Such a contaminated standard tile surface results in faulty on-sheet measurements of the color of the paper surface. In present systems, frequent cleaning of the standard tile is required and because of the inconvenience in gaining access to the tile for this purpose such cleaning is often not done with adequate frequency.

Sheet Stabilization

Color sensors include an optical sensing system disposed above the path of the moving sheet and a backing system positioned opposite the optical sensing system below the path of the sheet. As color sensors become more precise, the paper sheet must remain precisely positioned in relationship to the optical sensing system. In practice this means that the paper sheet must run along a backing tile at a very small, constant flying height. In some prior art color sensors, such as that disclosed in the aforementioned U.S. Pat. No. 3,936,189, the sheet rides in contact with the backing system, referred to as a "shoe", which functions to support the moving sheet at a reference position as it travels past the optical sensing system. Although such a support can provide a stable vertical position for the sheet within the gap (defined as the distance from the upper and lower heads carrying the sensing and backing systems) contact between the sheet and the "shoe" can cause tearing or marking of the sheet. Although attempts have been made to provide air cushions for non-contact measurements, these systems have not provided the necessary sheet stability and positional precision within the gap between the optical sensing head and the backing system. The inability to control sheet flutter reduces the accuracy of color measurements as a result of the sheet moving toward and away from the optical system and backing member.

SUMMARY OF THE INVENTION

Opacity Correction

The present invention provides for on-line measurements of the color and color-related properties of a moving sheet of material such as paper. According to one aspect of the present invention, there is provided an apparatus for making contrast ratio reflectance measurements from which opacity corrections may be made substantially in real time for a full color spectrum.

The color sensor of the present invention uses two independent but synchronized spectrometers, the first spectrometer being aligned to view a region of the sheet backed with a highly reflective ("white") material and the second spectrometer being aligned to view a region of the sheet backed with a highly absorptive ("black") material. Importantly, the use of spectrometers permits opacity corrections to be made for a full color spectrum. Moreover, because two independent devices are used, the "black" and "white" measurements can be performed at substantially the same time, eliminating the non-uniformity problem. Since the backing does not need to be moved between measurements, the instrument can perform measurements and opacity corrections substantially in real time, the rate being limited only by the performance of the optics and electronics, thus allowing very high update rates, generally sufficient to detect product non-uniformities such as streaks due to sizing adhesion problems.

Measurement of Fluorescent Properties

In accordance with another aspect of the present invention, there is provided an optical color sensing system including two sources, a flashlamp switched on and off and a tungsten filament lamp that is continuously energized.

Light from the flash lamp and tungsten filament lamp are combined by a beam splitter to illuminate the sheet. The beam splitter is selected so that the energy distribution of the combined beam approximates a standard source, preferably the D65 standard source. The balance of UV to visible light which characterizes such a standard source will change, however, as the lamps age. Pursuant to the present invention, the system computer is used to control the flashlamp intensity based on readings made on the standard fluorescent tile during the standardization time. Thus, the invention controls the amount of ultraviolet electronically under computer control. The present invention has no moving parts and takes advantage of the ease of computer control and the high stability of base spectrum illumination.

Protection of Standardizing Tile

In accordance with another aspect of the invention, during the standardization procedure, when the sensor is off-sheet, a lower sheet guide forming part of the backing system is lifted by means of a linear actuator against an upper sheet guide on the optical sensor housing so as to seal off the standard wheel. The wheel is free to rotate and expose the white standard tile to the upper optical sensing system without ever exposing the standard tile to the paper mill environment. Degradation of measurements is thus avoided and frequent cleaning of the standard tile is made unnecessary.

Sheet Stabilization

In accordance with another aspect of the present invention, the paper sheet flying height over a backing tile is so controlled that flutter, i.e., variations in the vertical position of the paper, is minimized. The flying height of the paper sheet is controlled by porting compressed air into a plenum chamber in the form of an annular groove formed in a paper guide comprising a circular plate. This air then flows through a series of slots cut tangentially into a circle around the backing tile. As a result of the high-speed circular or vortex flow and conservation of momentum, a low pressure area is formed in the annular region. This low pressure area draws the sheet down toward the upper surface of the plate along which surface the paper sheet travels. On the other hand, because of centrifugal force, the swirling air flow spirals outwardly over the surface of the plate thereby providing an air film between the sheet and the surface of the plate which effectively serves as an air bearing and which allows the paper to run very close to the standard along a stable passline without touching the tile. Sheet flutter is virtually eliminated. Since there is no contact between the sheet and the sheet guides, sheet breaks and marking of the sheet are also eliminated. The sheet stabilizer design is single sided, is not sensitive to scanner alignment and the airflow can be easily adjusted to control the magnitude of the force urging the sheet towards the guide plate. The air bearing reduces or eliminates wear and contaminate build-up on the backing which can be of critical importance for applications such as a color measurement. Since no "hold-down" rings or buttons are required on the upper head to keep the sheet in place, problems with sheet pinching or dirt build-up are avoided.

BRIEF DESCRIPTION OF THE DRAWINGS

Other objects, features and advantages of the present invention will become apparent from the detailed description of the invention, below, when read in conjunction with the accompanying drawings in which.

DETAILED DESCRIPTION OF THE PREFERRED EMBODIMENTS

Figure 1:
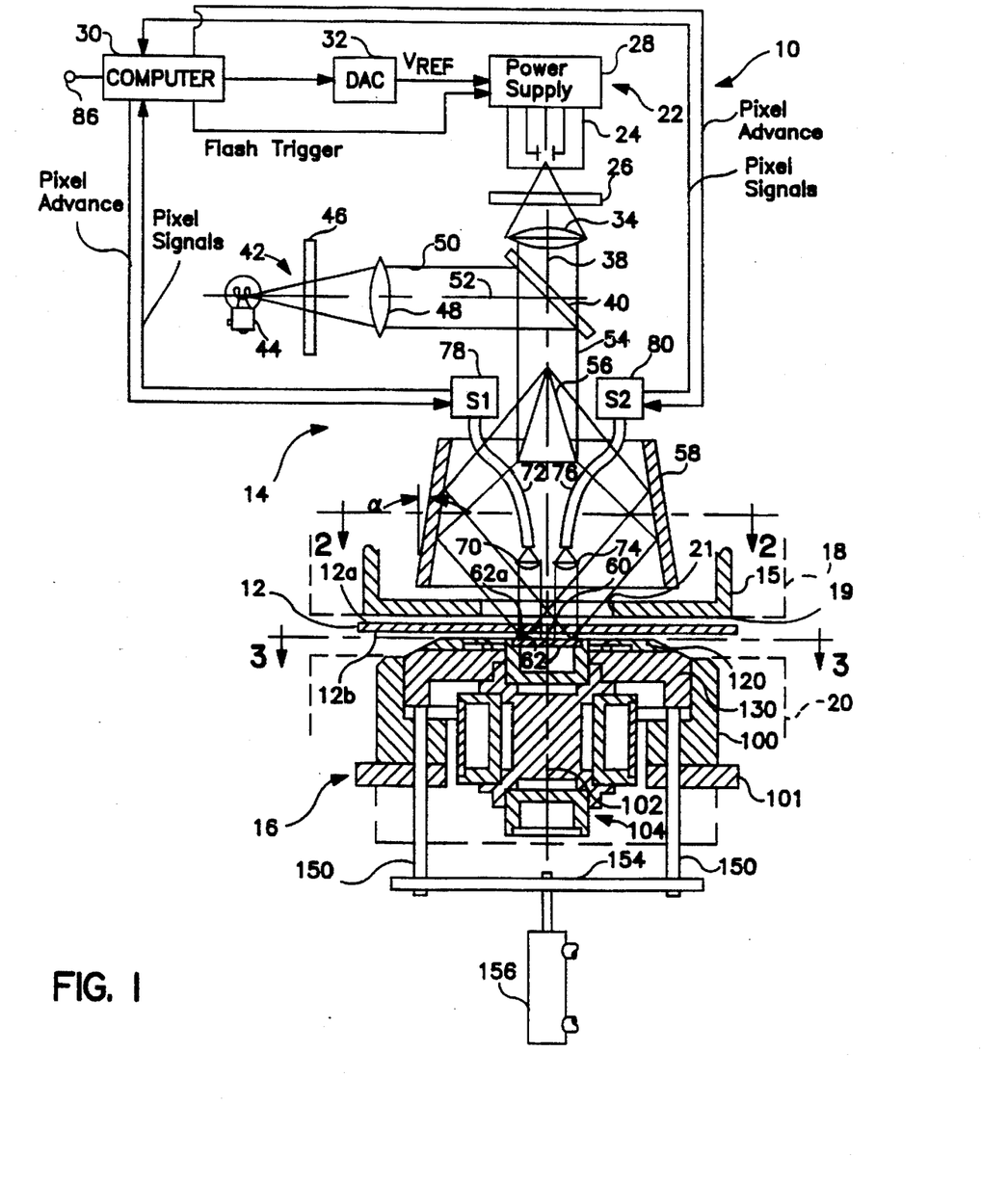
FIG. 1 is a schematic, front elevation view, partly in section, of a sensor system in accordance with the present invention.

FIG. 1 shows a sensor system 10 in accordance with a preferred embodiment of the invention for measuring on-line the color and color-related properties of a moving sheet of material 12, such as paper, during its fabrication. The sheet has a top surface 12a and a bottom surface 12b. The color sensor system 10 includes an optical sensing system 14 disposed above the paper sheet 12 and a backing system 16 positioned under the sheet. In a manner well known in the art, the optical sensing system 14 is mounted in a housing 15 carried by in the upper head 18 (a portion of the outline of which is shown in broken lines) of a conventional scanner while the backing system 16 is carried by the lower head 20 (also shown in broken lines) of the scanner. The scanner heads 18 and 20 are driven in unison back and forth across the width of the sheet in a direction transverse to the direction of sheet travel. The housing 15 has a lower planar sheet-guide surface 19 and a central opening 21.

The optical system 14 has a first light source 22 for periodically illuminating the paper sheet 12. The source 22 includes a xenon flashlamp 24 and band pass filter 26 for transmitting energy substantially only in the ultraviolet excitation band of fluorescent whitening agents. The flashlamp 24 is turned on and off rapidly, for example, at 50 Hz, by a power supply 28 controlled by a computer 30 coupled to the supply 28 through a digital-to-analog converter (DAC) 32. As will be described in greater detail below, the computer 30 controls the charge on a capacitor (which is triggered to discharge at a flashrate of 50 Hz) and hence the amplitude or intensity of the light produced by the flashlamp 24. Light transmitted by the filter 26 passes through condenser lens 34 to form a collimated light beam 36 along a vertical optical beam axis 38. A portion of the beam 36 passes through a beam splitter 40 where it is combined with light from a second light source 42. The light source 42, which produces light principally in the visible wavelength range, comprises a continuously energized tungsten filament quartz-halide lamp 44 and color correcting filter 46 which balances the spectrum of light emitted by the lamp 44 to approximate the CIE standard illuminant "C". Collimating optics 48 adjacent the filter 46 forms a beam 50 directed toward the beam splitter 40 along the horizontal optical beam axis 52 perpendicular to the axis 38. By way of example, the optics 48 may take the form of a lens or a parabolic mirror behind the lamp 44.

The UV and visible light beams from the sources 22 and 42 transmitted and reflected, respectively, by the beam splitter 40 form a combined beam 54 along the vertical axis 38. The combination of filters 26 and 46, flashlamp voltage and beam splitter 40 is chosen to provide approximately the right balance of ultraviolet wavelengths to visible wavelengths so that the combined beam 54 approximates the energy distribution of the D65 illuminant standard. During the time that the source 22 is off, the beam 54 will, of course, contain only the light energies produced by the continuously energized second source 42 as modified or redistributed by the beam splitter 40.

Figure 2:
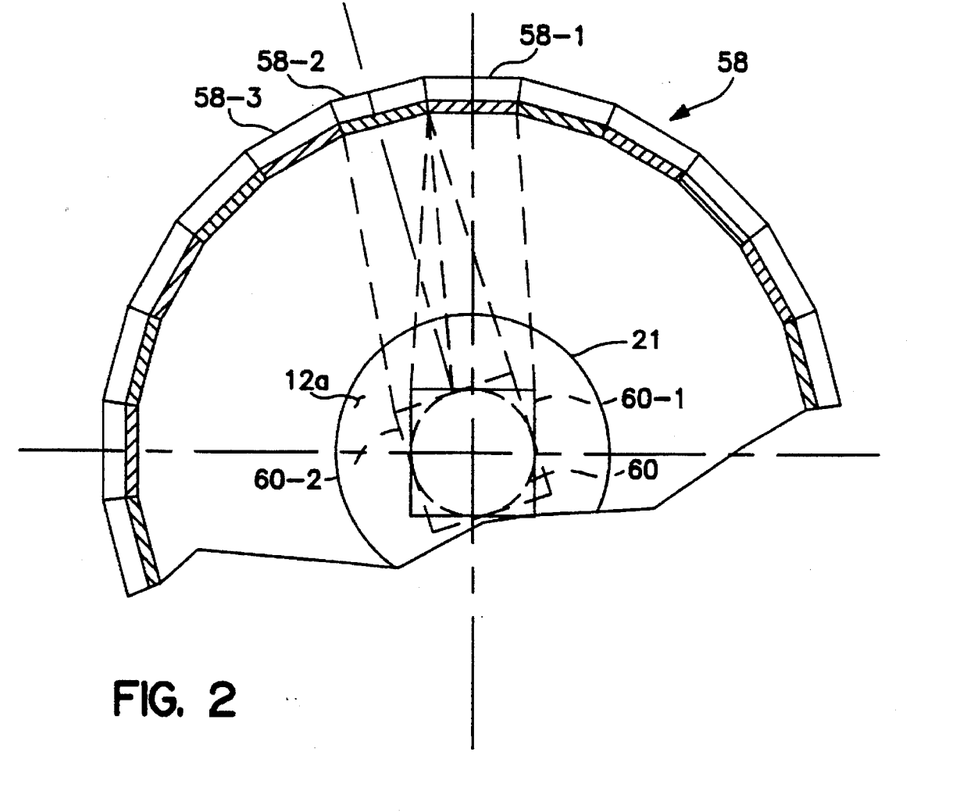
FIG. 2 is a cross section view of the system of FIG. 1 as seen along the line 2—2.

The combined beam 54 is reflected by the outer surface of a mirror 56 in the shape of a right circular cone whose central, vertical axis is coincident with the beam axis 38 and whose apex subtends an angle of, for example, about 24.5°. The conical mirror directs the rays outwardly at about 49° relative to the central axis 38. The rays are then reflected inwardly toward the sheet 12 at an angle of approximately 45° to the plane of the paper 12 by means of a multi-faceted or polygonal mirror 58. It will be evident to those skilled in the art that other geometries may be employed so long as the final angle is approximately 45°. The mirror 58 is in the form of the frustrum of a regular pyramid converging as shown in FIG. 1 and having a vertical central axis coincident with the beam axis 38. With reference now also to FIG. 2, in accordance with a preferred embodiment of the invention, the mirror 58 has twenty-four lateral faces 58-1, 58-2, 58-3, and so forth, inclined inwardly at an angle, $\alpha$, of about 2°. The light reflected by the multifaceted mirror 58 passes through the housing opening 21 and converges onto a generally circular area 60 of illumination on the paper surface 12a. This mirror geometry provides uniform light distribution in the sample region 60 with excellent optical efficiency. The n-sided pyramidal mirror 58 is an improvement over the standard "axicon" optics geometry which uses a cylindrical or conical mirror and avoids the tendency of the axicon optics arrangement to produce a bright spot at the center of the area of illumination. As shown in FIG. 2, each face 58-n of the mirror 58 reflects light from the conical mirror 56 to illuminate a generally trapezoidal area 60-n on the surface 12a of the paper, the width of which is approximately twice the width of a mirror facet and the length of which is proportioned to the diameter of collimated beam 54. With correct choice of these parameters, each facet completely illuminates the viewing area 60. The overlapping areas 60-1 and 60-2 illuminated by the faces 58-1 and 58-2 of the polygon mirror overlap, as shown in FIG. 2 for the two mentioned mirror faces, so that the net effect of the illumination provided by all of the faces of the mirror 58 is the circular area 60 having a substantially uniform light distribution.

Figure 3:
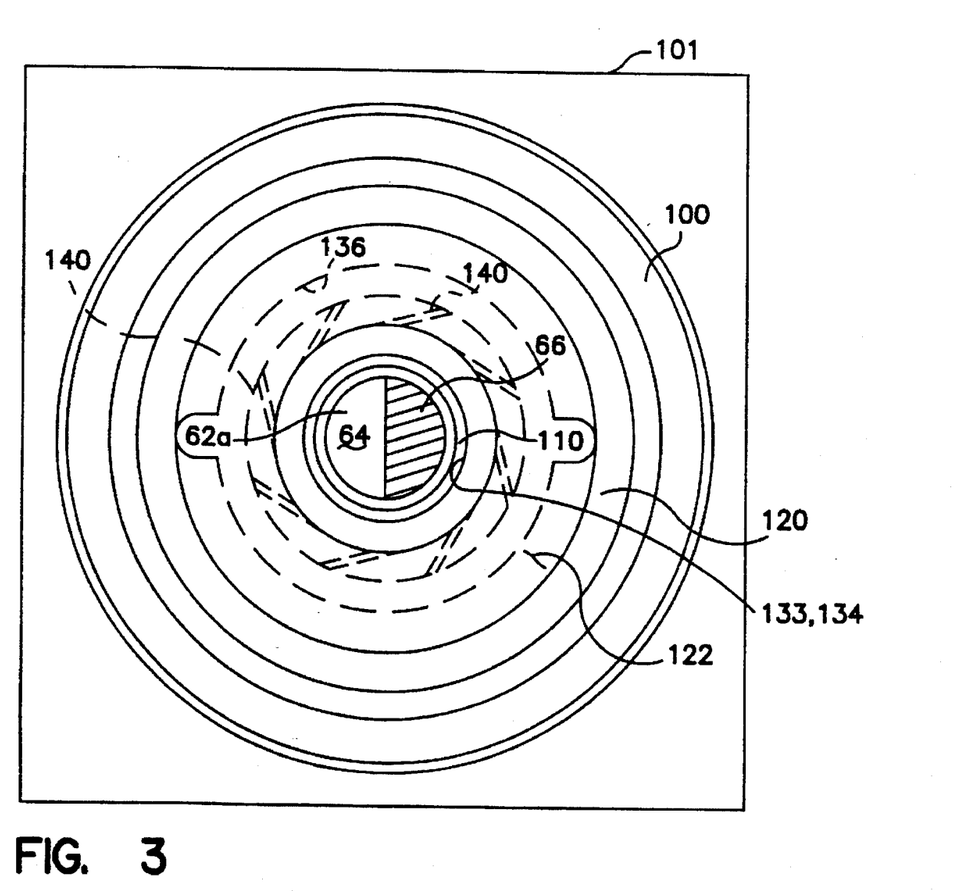
FIG. 3 is a top, plan view of a sheet backing system in accordance with the present invention, as seen along the line 3—3 in FIG. 1.

Because paper is typically translucent, a portion of the light incident on the sheet 12 is transmitted through the sheet and another portion of the light is reflected from the sheet surface 12a. The portion of the light transmitted through the sheet 12 falls upon the top surface 62a of a tile 62 adjacent the bottom surface 12b of the sheet. The tile 62 serves as the backing element during on-sheet measurements by the color sensor. As shown in FIG. 3, the measure tile 62 has a segmented surface one half (64) being substantially reflective ("white") and the other half (66) being substantially absorbing ("black"). The use of a segmented black/white backing together with dual spectrometers (as will be described) allows simultaneous measurements of sheet reflectivity at multiple wavelengths. The Kubelka-Munk formulae or other known methods may then be used by the computer 30 to compute a transparency compensation to arrive at the "infinite pad" reflectivity at each wavelength from the reflectivities at each wavelength measured for the sheet backed with "black" and "white" backings. (The correction algorithm does not require "black" or "white" to be perfectly absorbing and reflecting, only that their respective reflective spectra are known.) Such simultaneous measurement with both "black" and "white" backings ensures that changes in sheet transparency over time does not affect the determination of infinite pad reflectance. Correction is made using the reflectivities measured by the dual spectrometers at each wavelength, which is superior to using a single "opacity" correction since transparency is wavelength dependent.

Figure 4:
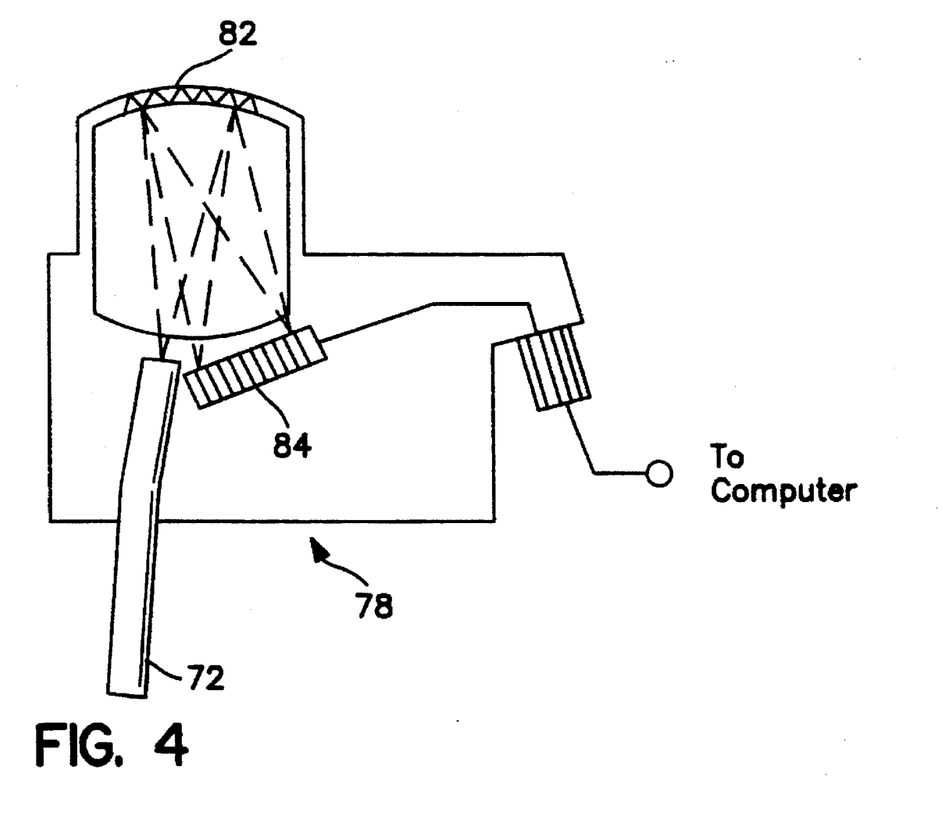
FIG. 4 is a schematic diagram of a spectrometer that may be used in connection with the present invention.

The optical sensing system 14 also includes a lens 70 positioned above the sheet 12 in vertical alignment with the white segment 64 of the measure backing tile 62. The lens 70 collects the portion of light reflected by the top sheet surface 12a together with the portion of the light transmitted through the sheet and reflected by the white part of the tile and retransmitted through the sheet. The total reflected light (having a bright reflectance intensity) is focused by the lens 70 on the end of a first fiber optics bundle 72. Similarly, a lens 74 in vertical alignment with the black segment 66 of the measure tile 62 collects the total reflected light (having a dark reflectance intensity) emitted by the portion of the sheet overlying the black segment 66 and focuses it on the end of a second fiber optics bundle 76. The fiber optical bundles 72 and 76 transmit light to first and second spectrometers 78 and 80, respectively. With reference now also to FIG. 4 which shows a schematic representation of the spectrometer 78, each of the spectrometers 78 and 80 may be a commercially available unit such as the Zeiss Miniature Monolithic Spectrometer (MMS), an exceedingly compact unit incorporating a diffraction grating 82 that separates light incident thereon into its component wavelengths and a linear photodetector array 84 which produces an electrical representation of the intensity distribution of the different portions of the spectrum.

Generally, the video or pixel outputs of the detectors of the spectrometers 78 and 80 (also denoted as S1 and S2 in FIG. 1) are clocked by logic on the computer processor board into an ADC and stored sequentially in random access memory. The digitization sequence, which proceeds at a 200 kHz rate, interleaves the two spectrometer video readouts: S1/Pixel1, S2/Pixel1, S1/Pixel2, S2/Pixel2, and so forth. This results in measurement of the spectra from spectrometers 78 and 80 simultaneously within 5 µsec.

Figure 5:
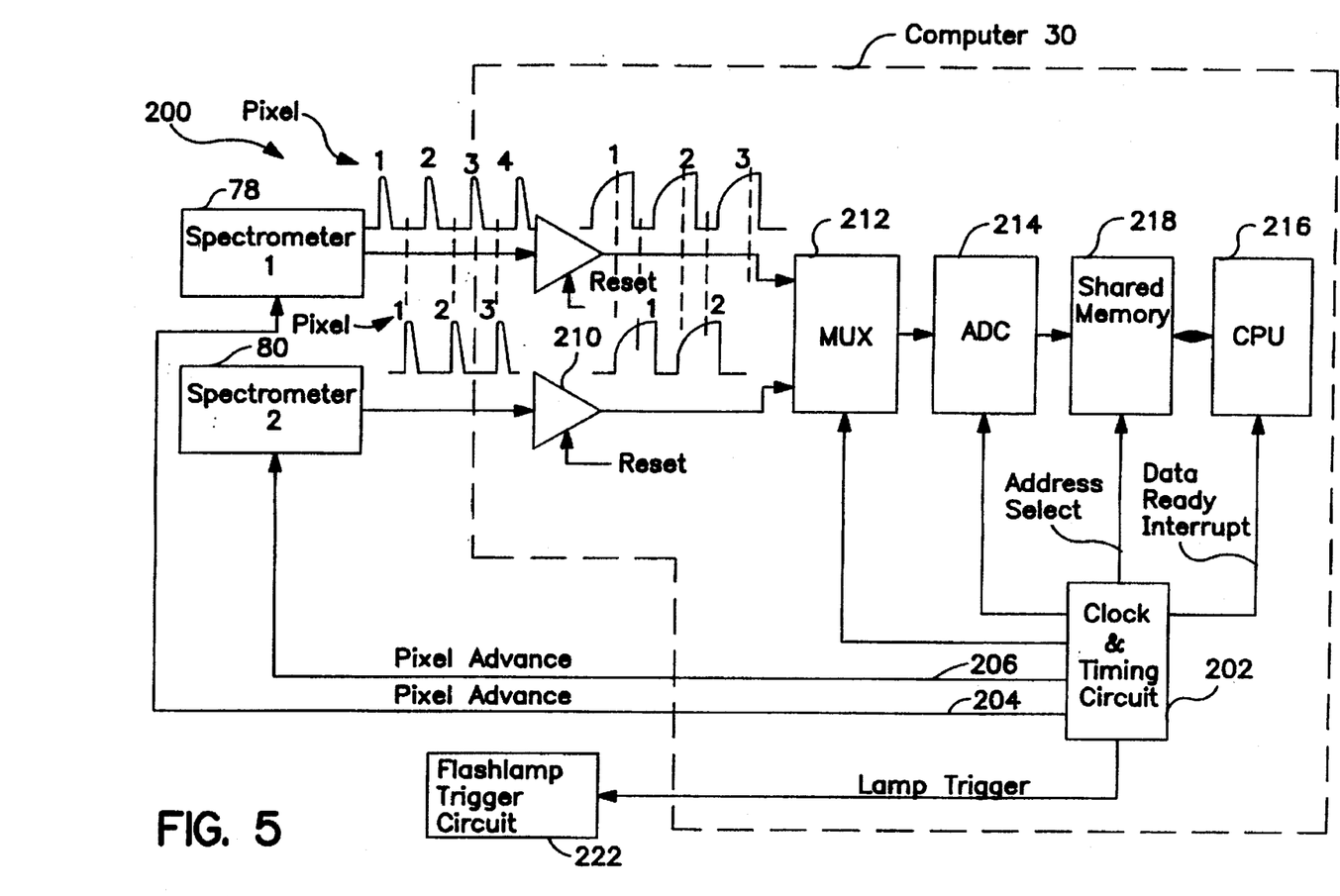
FIG. 5 is a block diagram of a circuit for controlling synchronization of the spectrometer.

More specifically, the linear photodetector array 84 (FIG. 4) comprises a series of diodes each of which generates an analog electrical or pixel signal the magnitude of which corresponds to the intensity of light in the range of wavelengths directed to that particular diode. The photodetector array of each spectrometer is arranged to provide an output in the form of a serial stream of pixel signals. FIG. 5 shows schematically a data acquisition logic circuit 200 for processing and synchronizing the outputs of the spectrometers 78 and 80 and for providing a flashlamp trigger signal. The circuit 200 includes a clock and timing circuit 202 having a pair of outputs 204 and 206 providing synchronizing pixel advance signals to the photodetector arrays of the spectrometers 78 and 80. The pixel advance signals alternately clock out the pixel output signals from the spectrometers. The pixel signals from each spectrometer are integrated by resettable pulse integrators 208 and 210 and are alternately applied to a multiplexer 212 controlled by a clock signal from the clock and timing circuit 202. Pixel signals produced by the two spectrometers alternately appear at the output of the multiplexer and are converted to digital form by an analog-to-digital converter 214. The digitized pixel signals are stored in a shared memory 218 whose pointer is advanced by the clock and timing circuit 202 after each digitized pixel signal is stored. The clock and timing circuit 202 resets each pulse integrator 208, 210 after each conversion by the ADC 214. The clock and timing circuit 202 interrupts the microprocessor 216 when the entire spectra for both spectrometers have been converted and stored in memory. The computer 30 then analyzes the digitized signal arrays and computes the reflectance for each wavelength for each of the two ("black" and "white") backing conditions and the true color of the paper. An output 86 (FIG. 1) from the computer 30 can be used to control the color of the paper being produced.

As already indicated, the optical components are selected so as to provide a combined beam 54 from the sources 22 and 42 having a distribution of energy that approximates the D65 standard source. This distribution will change, however, as the lamps 24 and 44 age resulting in a change in the energy distribution manifested by change in the UV-to-visible light balance of the combined beam 54. In accordance with one aspect of the invention, the computer 30 is used to control the intensity of the flash from the flashlamp 24 and therefore the amount of UV radiation based on readings made on the standard fluorescent tile during the off-sheet standardization procedure.

Generally, the intensity of the flashlamp flash is determined by the voltage applied to the flashlamp 24. The flashlamp power supply charges an energy storage capacitor to a voltage proportional to a control voltage, Vref. The computer outputs Vref to the lamp power supply by means of a DAC. In this fashion the amount of UV may be tuned to maintain a UV to visible light balance consistent with the standard source (D65) wavelength distribution or any other desired illuminant distribution.

Figure 6:
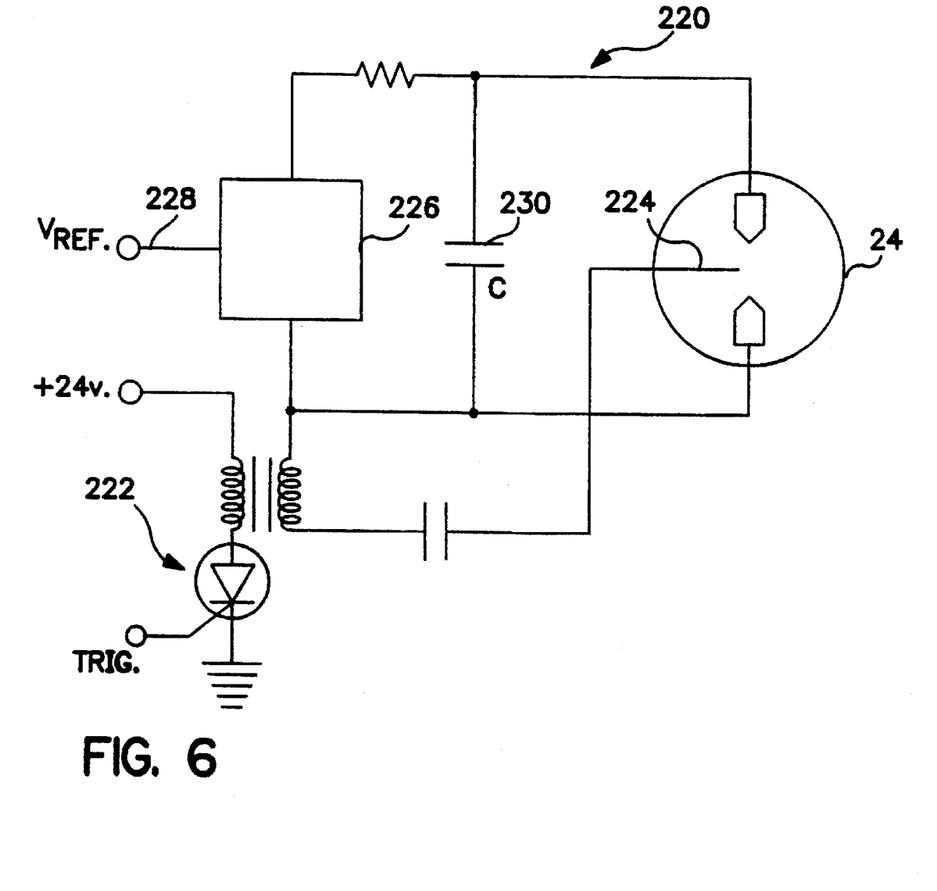
FIG. 6 is a schematic diagram of a circuit for controlling the energization of a flashlamp.

A preferred embodiment of a capacitance discharge circuit 220 for controlling the intensity of the flashlamp 24 is shown in FIG. 6. This circuit includes an SCR flashlamp trigger circuit 222 controlled by trigger signals generated by the clock and timing circuit 202 (FIG. 5). The trigger circuit 222 is connected to the trigger electrode 224 of the flashlamp 24. The circuit 220 includes a high voltage generator 226 for producing an output signal proportional to the reference voltage Vref applied to an input 228 of the high voltage generator 226. By way of example, a five volt signal at the input of the high voltage generator produces 500 volts at the output terminals of the generator. This output voltage charges a capacitor 230 with an energy proportional to the square of the output voltage which in turn is proportional to Vref. A trigger pulse from the flashlamp trigger circuit 222 initiates the breakdown in the gap of the flashlamp 24 and the stored energy in the capacitor 230 is discharged in the flashlamp plasma.

The output from the digital-to-analog converter 32 (FIG. 1) supplies the reference voltage, Vref, to the high voltage generator 226. This reference voltage may be selected for flashlamp voltage control in several ways. For example, at the time the sensor 10 is standardized off-sheet, a tile with a known amount of fluorescence is measured. If the measured value is less than the known amount, then the output of DAC 32 is increased by the computer 30. If more than the known amount is measured then the DAC output is decreased. If necessary, after the first adjustment the measurement can be repeated until agreement is reached. In practice it is usually possible to predict the correct adjustment on a single iteration. Alternatively, a pair of diodes, one with a wavelength selecting filter for the UV and the second with a filter for the blue, monitor the incident light. The ratio of the UV to blue intensities obtained either electronically or by computer calculation can be used to control the lamp voltage to hold the UV to blue ratio at a preselected value.

Figure 7:
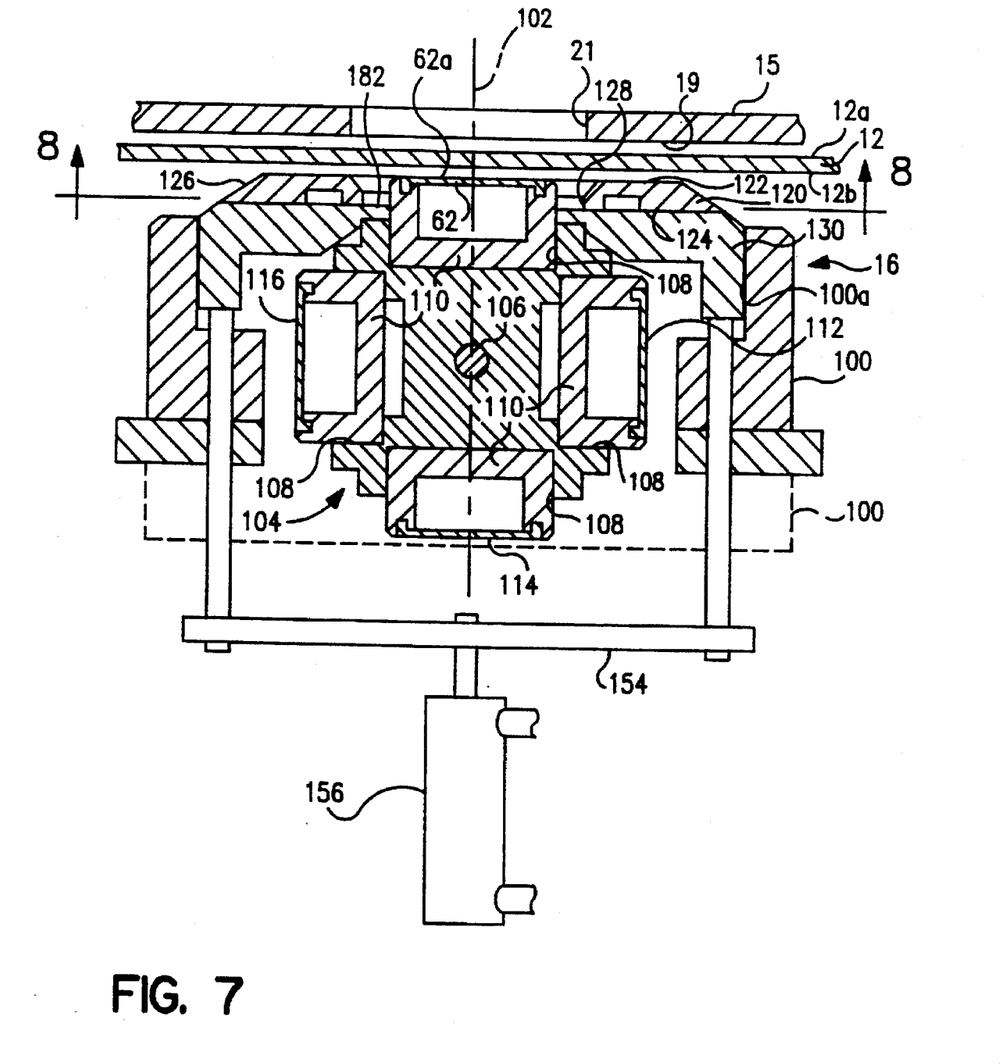
FIG. 7 is a front elevation view, in section, of a backing system in accordance with the present invention in which the backing system is shown in its on-sheet measurement configuration.
Figure 10:
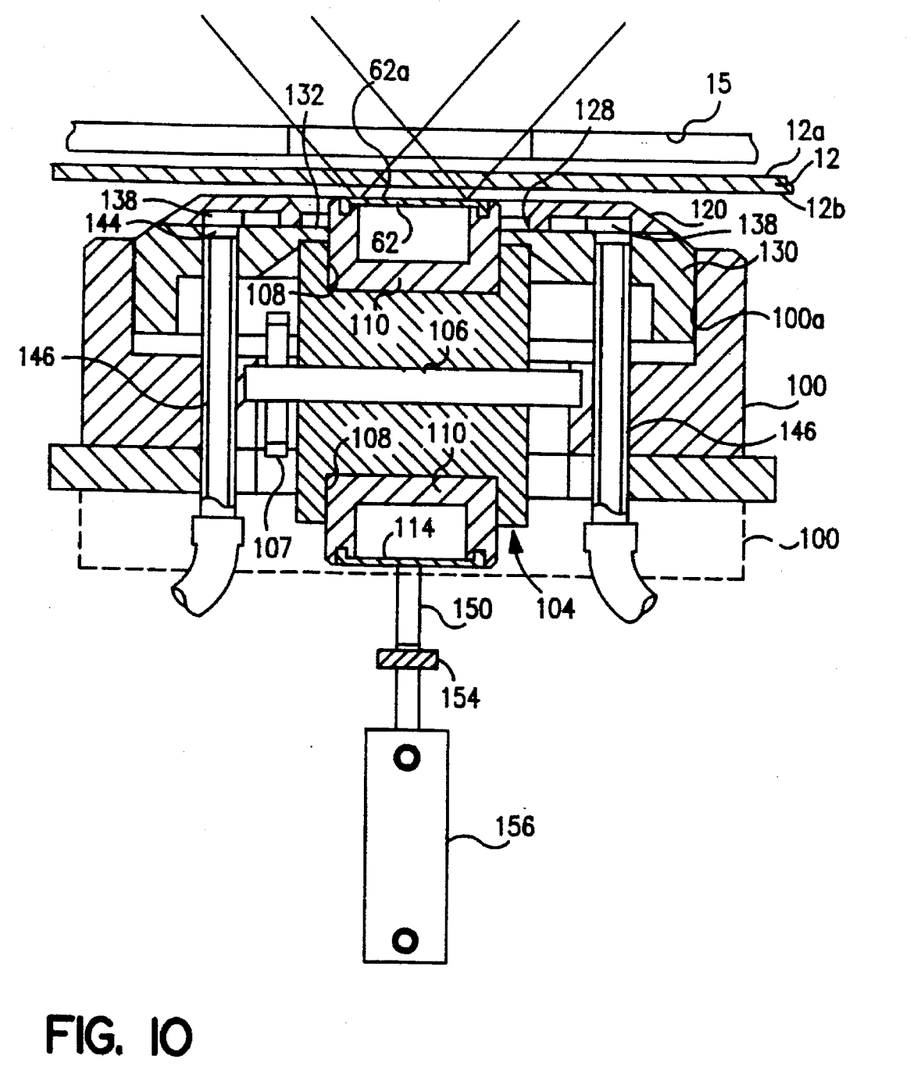
FIG. 10 is an end elevation view, in cross section, of the backing system of FIG. 7 showing certain details of a sheet stabilizer in accordance with another aspect of the invention.

The backing system 16 includes an outer, generally cylindrical casing 100 secured to the lower scanner head 20 by means of a square base 101. The cylindrical housing has a vertical central axis 102. When the scanner heads 18 and 20 are properly aligned, the axis 102 of the outer cylinder casing 100 is in alignment and coincides with the vertical optical axis 38. Mounted inside the outer casing 100 is a backing wheel 104 rotatable about a horizontal shaft 106 by means of a stepper motor (not shown) coupled to a drive gear 107 mounted on the shaft 106 (FIGS. 7 and 10). The backing wheel 104 has identical bores 108 spaced equiangularly about the shaft 106 and each of which receives a cylindrical, cup-shaped insert 110 carrying a disk shaped standardizing tile about the open end thereof. These tiles include the above-mentioned black/white measure tile 62; a white standard tile 112; a verification tile 114; and a white fluorescent standard tile 116. The backing wheel 104 is rotatable by the stepper motor to four discrete positions for bringing the various tiles into the uppermost position adjacent the sheet passline.

The backing system 16 further includes a sheet guide 120 in the form of a circular plate having an upper horizontal sheet guide surface 122, a lower surface 124, a beveled outer edge 126 and a central, circular opening 128. The sheet guide is secured to a cylindrical base plate 130 including an inwardly projecting flange 132 (FIG. 9) having an inner surface 133 defining a central opening 134 (FIG. 3) concentric with the opening 128 in the sheet guide 120 but having a smaller diameter than that of the opening 128. The diameter of the opening 134 is approximately the same as the outer diameter of the inserts 110, which are identical, so as to permit an insert to project upwardly through the opening 134 with minimum clearance between the insert and the inner flange surface 133 to prevent debris from entering the interior of the casing. In this connection, it will be understood that the outer casing extends about the backing wheel 104, as shown by the broken lines (FIG. 7). In this fashion, the standard tiles are protected from the mill environment during on-sheet measurements.

Figure 8:
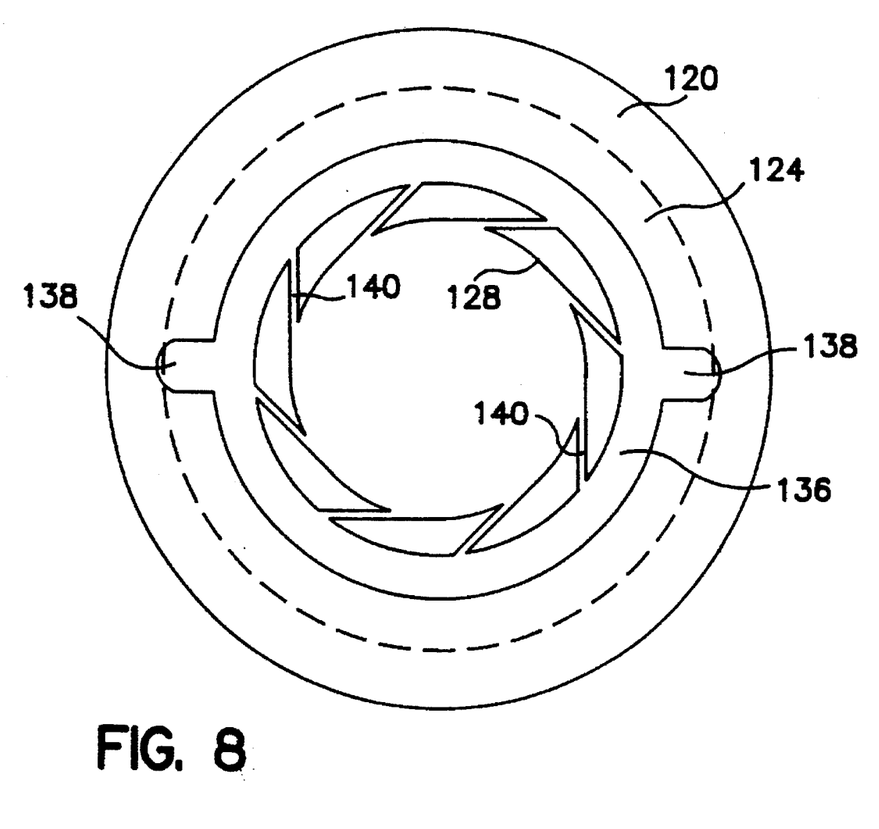
FIG. 8 is bottom view of a guide plate forming part of the sheet stabilizer of the invention, as seen along the line 8—8 in FIG. 7.

As best seen in FIG. 8, formed in the lower surface 124 of the sheet guide 120 is a circular groove 136. Also formed in the lower surface 124 is a pair of diametrically opposed recesses 138 each opening into the circular groove 136. A plurality of narrow passages in the form of bores, or preferably, slits 140 oriented substantially tangent to the central opening 128 provide communication between the groove 136 and the opening 128. In the embodiment shown in the drawings, eight (8) slits 140 are provided.

Figure 9:
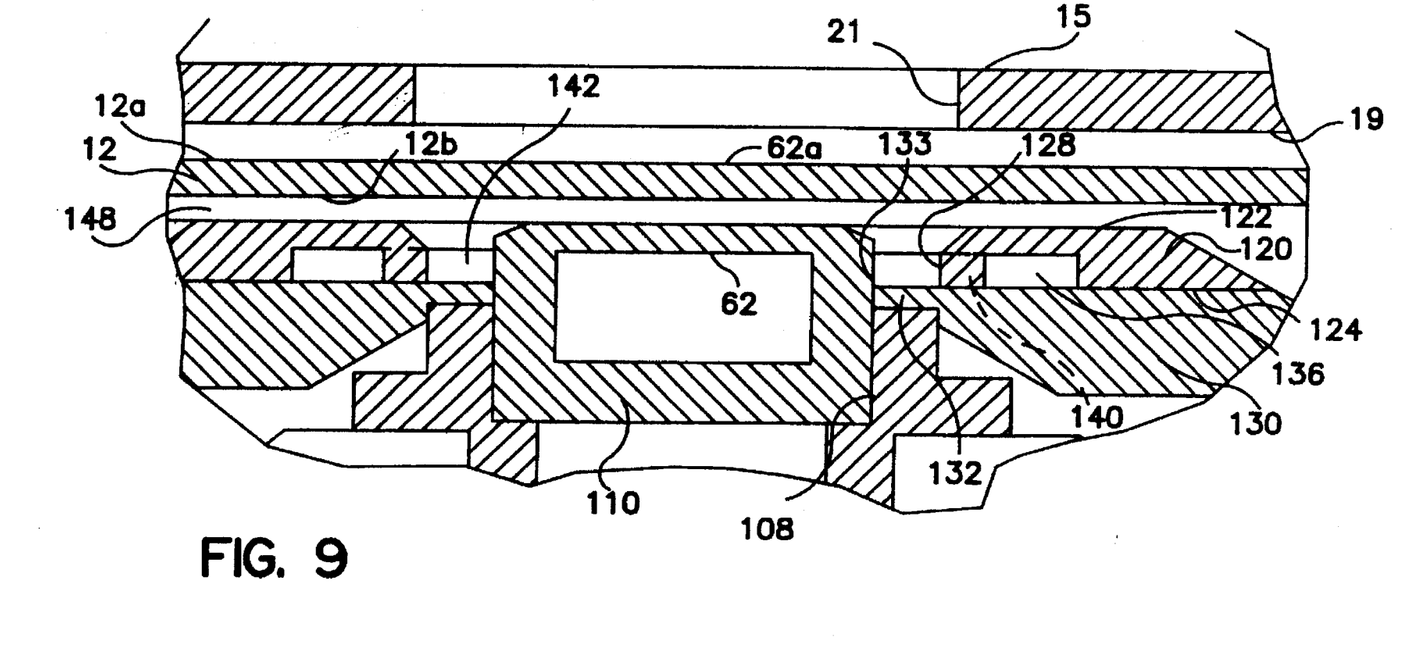
FIG. 9 is an enlarged front elevation view, in cross section, to show more clearly certain features of the sheet stabilizer of the present invention.

As best seen in FIGS. 1, 2, 4, 7 and 10, in the on-sheet measurement configuration of the backing system 16, the insert 110 carrying the black/white measure tile 62 is in its operational position, projecting through the flange opening 134 with the upper surface 62a of the tile 62 flush or coplanar with the upper guide surface 122 of the sheet guide 120. In this on-sheet measurement configuration of the backing system 16, an annular space 142 is defined between the outer surface of the insert 110 and the guide plate central opening 128 (FIG. 9).

With reference to FIG. 10, the base plate 130 includes diametrically opposed air inlet ports 144 in communication with the recesses 138 in the sheet guide 120. Each port 144 is connected by a tube 146 to a pressurized air supply (not shown).

With the color sensor in its on-sheet, measure configuration, air introduced under pressure through the ports 144 flows, via the circular groove 136 and tangential slits 140 into the annular space 142 around the tile support insert 110. The tangential orientation and small cross-sectional area of the slits 140 impart a high speed circulatory flow to the air in the annular space 142. As the result of conservation of momentum, a low pressure area is formed in the central portions of the vortex, that is, in the region immediately about the backing tile insert 110. This low pressure area causes the portion of the paper sheet overlying the tile to be urged down toward the outer tile surface 62a. At the same time, however, the centrifugal forces acting on the circulating air in the annular space 142 causes air to escape and spiral outwardly along the upper sheet guide surface 122. The result is an equilibrium in the position of the paper, with a thin air film or air bearing being present in a gap 148 (FIG. 9) between the bottom surface 12b of the paper sheet on the one hand and the sheet guide and standard tile surface 62a on the other. Thus, the paper surface 12b runs very close to the measure tile surface 62a without contacting it along a sheet passline that is highly stable, i.e., subject to minimum flutter. The thickness of the air film can be readily controlled by adjusting the air flow into the ports 144 by means of a needle valve or the like (not shown). The sheet stabilizer of the invention is single sided and the reduced pressure around the tile insert 110 prevents any dirt or debris from entering the housing 100 via any small gap that may exist between the insert 110 and the inner surface 133 of the flange 132.

Figure 11:
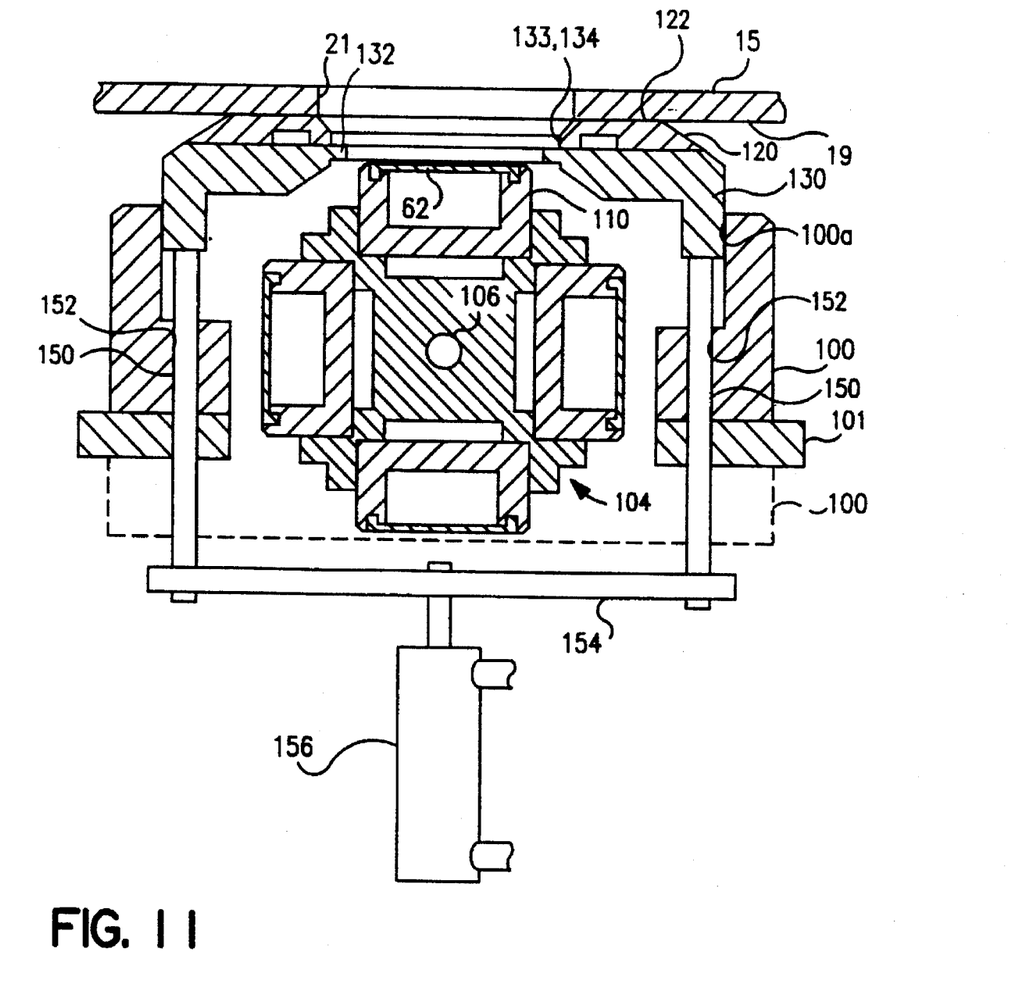
FIG. 11 is a front elevation view, in section, of the backing system of FIG. 7 in which the backing system is shown in its off-sheet, standardizing configuration.

Provision is also made to facilitate rotation of the backing wheel 104 and to standardize the sensor off-sheet while maintaining isolation of the white standard tile from the paper mill environment. In this connection, the cylindrical base plate 130 is slidably received within a bore 100a formed in the casing 100. The base plate 100 thus forms a piston vertically displaceable within the bore 100a. The base plate 130 is mounted on a pair of connecting rods 150 slidably received in vertical bores 152 formed in the casing 100 (FIG. 11). The rods 150 are secured at their lower ends to a cross member 154 which in turn is connected to the piston of a pneumatic cylinder 156. Accordingly, up and down displacement of the piston will cause a corresponding vertical displacement of the base plate 130 and sheet guide 120. During on-sheet measurements, the piston in the cylinder 156, and hence the sheet guide 120, are in their retracted positions as shown, for example, in FIGS. 1, 7, 9 and 10 with, as already stated, the top surface 62a of the measure tile 62 being coplanar with the sheet guide upper surface 122.

Figure 12:
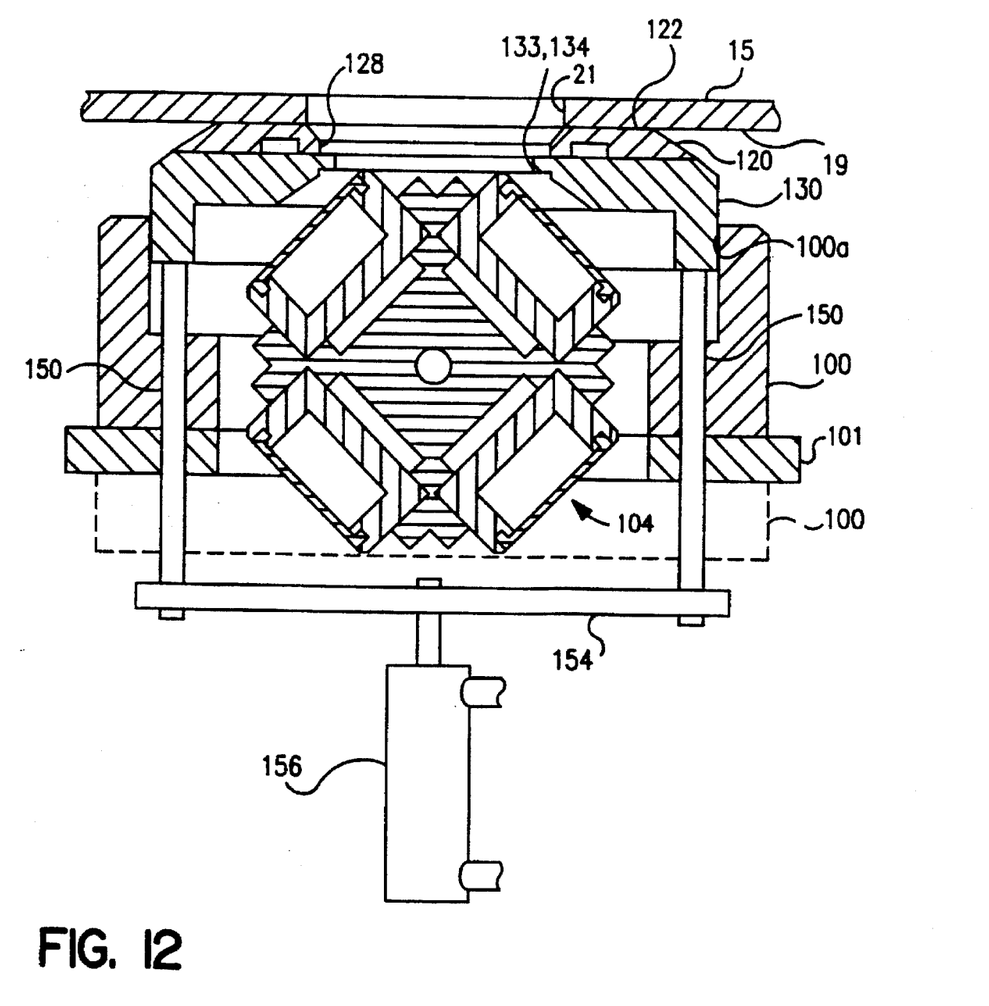
FIG. 12 shows the backing system of FIG. 7 during the off-sheet standardizing procedure in which the backing wheel is in the process of rotating from one standardizing tile position to another.

In preparation for standardization, the scanner heads are moved off-sheet, that is, to an extreme position of their travel beyond one or the other side edge of the sheet 12. With reference now to FIG. 11, once the scanner heads are in the standardization position, compressed air is ported to the pneumatic cylinder 156 thereby raising the sheet guide 120 against the lower guide surface 19 surrounding the opening 21 in the optical sensor housing 15 thereby effectively sealing off the backing wheel 104. With the measure tile insert 110 now free of the constraint of the base plate opening 134, the backing wheel 104 is free to be rotated, as shown in FIG. 12, to expose the surface of the white standard tile 112 to the optical sensing system 14 without exposing the white tile to the paper mill environment. In this fashion, the white tile 112 is at all times—during on-sheet measurement as well as during off-sheet standardization—isolated from the ambient contaminating environment of the paper mill.

Various standard tiles can be rotated into reflectance measuring position during standardizing. When the standardizing procedure is complete, the backing wheel 104 is rotated by the stepping motor to bring the measure tile 62 to the top position. The pneumatic cylinder 156 is actuated to retract the sheet guide 120 to its on-sheet position (for example, FIGS. 1 and 7) so that scanning of the paper sheet can once again take place.

What is claimed is:

1. A sensor for measuring on-line selected properties of an area of a sheet having opposed surfaces and being movable relative to the sensor, the sensor comprising:

at least one light source adjacent one of the sheet surfaces for illuminating said area of said sheet;

a backing having a surface adjacent the other surface of the sheet, said backing surface being positioned to receive illumination from said at least one source transmitted through said area of said sheet, the backing surface including first and second regions having known, substantially different reflectivities;

a first spectrometer positioned to view a portion of said area of said sheet backed by the first region of the backing surface;

a second spectrometer positioned to view a portion of said area of said sheet backed by the second region of the backing surface; and means connected to said first and second spectrometers for synchronizing the spectrometers to measure spectra at substantially identical times.

2. A sensor, as defined in claim 1, in which:

each spectrometer includes a detector for producing an output comprising a serial stream of electrical pixel signals, each signal having a magnitude corresponding to the intensity of light in a predetermined range of wavelengths comprising a portion of the detected spectrum, said synchronizing means including means for clocking said spectrometer outputs to alternate the output of said pixel signals from said spectrometers, and a memory for storing said pixel signals.

3. A sensor, as defined in claim 1, including:

signal processing means connected to said spectrometers, the processing means including means for calculating the infinite pad spectral reflectivity derived from substantially measuring values for spectral reflectivity of the portions of the sheet backed by the first and second backing surface regions.

4. A sensor, as defined in claim 1, further including:

a mirror for receiving light from said at least one source and oriented to reflect said light to illuminate said area of said sheet, said mirror comprising a plurality of substantially planar faces, each face reflecting a portion of the light from said source to illuminate a portion of said area.

5. A sensor, as defined in claim 4 in which:

the faces of the mirror are disposed symmetrically about said area.

6. A sensor, as defined in claim 5, in which:

the mirror comprises 24 faces.

7. A sensor, as defined in claim 5, which includes:

a second mirror interposed optically between said at least one source and said first-mentioned mirror, said second mirror being positioned to receive light from said at least one source along a beam axis and having a reflective surface for directing said light outwardly from said beam axis, the first-mentioned mirror receiving light from said second mirror and reflecting said light inwardly toward said beam axis.

8. A sensor, as defined in claim 7, in which:

the second mirror has a reflecting surface in the shape of a right circular cone having a central axis coincident with said beam axis and in which the faces of the first-mentioned mirror are arranged in the form of a frustrum of a regular pyramid having a central axis of symmetry coincident with said beam axis.

9. A sensor, as defined in claim 1, in which:

each spectrometer includes a detector array for producing a series of output signals, each output signal having a magnitude corresponding to the intensity of light in a predetermined range of wavelengths comprising a portion of the detected spectrum, said synchronizing means comprising means for synchronizing the output signals from said detector arrays.

10. A sensor, as defined in claim 9, in which:

the output signal synchronizing means interleaves the output signals from the detector arrays of the first and second spectrometers.

11. A sensor, as defined in claim 4, in which:

the faces of the mirror are arranged in the form of a frustrum of a regular pyramid.

* * * * *